(12) United States Patent
Pak et al.

(10) Patent No.: US 8,216,614 B2
(45) Date of Patent: Jul. 10, 2012

(54) POWDER MIX OF POTASSIUM CALCIUM CITRATE FOR THE TREATMENT OF KIDNEY STONES AND OSTEOPOROSIS

(75) Inventors: Charles Y. C. Pak, Dallas, TX (US); Khashayar Sakhaee, Dallas, TX (US); Neill B. Walsdorf, Sr., San Antonio, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 0 days.

(21) Appl. No.: 12/784,305

(22) Filed: May 20, 2010

(65) Prior Publication Data

US 2010/0227006 A1    Sep. 9, 2010

Related U.S. Application Data

(62) Division of application No. 11/183,140, filed on Jul. 15, 2005, now abandoned.

(51) Int. Cl.
*A61K 33/24* (2006.01)
*A61K 33/06* (2006.01)
*A61K 33/10* (2006.01)
*A61K 33/08* (2006.01)
*A61K 31/19* (2006.01)

(52) U.S. Cl. ........ 424/653; 424/682; 424/686; 424/687; 424/691; 514/574

(58) Field of Classification Search ............ 424/653, 424/682, 686, 687, 691; 514/574
See application file for complete search history.

(56) References Cited

U.S. PATENT DOCUMENTS 6,287,607 B2 * 9/2001 Pak et al. ............ 424/682
6,599,544 B2 * 7/2003 Buddemeyer et al. ....... 426/74
7,052,725 B2 * 5/2006 Chang et al. ............ 426/74

* cited by examiner

*Primary Examiner* — Kevin E Weddington
(74) *Attorney, Agent, or Firm* — Fulbright & Jaworski L.L.P.

(57) ABSTRACT

A composition comprising a powder mixture of potassium citrate and calcium citrate as mixtures of pure chemical salts and methods of making and using the composition are disclosed. The composition is useful for the treatment and prevention of kidney stones and osteoporosis and better delivers potassium and calcium than commonly used potassium and calcium supplements.

26 Claims, 7 Drawing Sheets

POWDER MIX OF POTASSIUM CALCIUM CITRATE FOR THE TREATMENT OF KIDNEY STONES AND OSTEOPOROSIS

This application is a divisional application of, and claims priority to, U.S. patent application Ser. No. 11/183,140, filed on Jul. 15, 2005 now abandoned.

TECHNICAL FIELD

A method is presented for making a powder formulation of potassium calcium citrate as mixtures of pure chemical salts, to be dissolved before ingestion, the said formulation yielding identical amounts of potassium and calcium and the same or slight excess of citrate, as delivered by potassium citrate and calcium citrate at doses commonly prescribed for the treatment of kidney stones and osteoporosis.

BACKGROUND OF THE INVENTION

Mineral compositions are commonly taken as dietary aids, either as therapeutic preparations directed to a specific medical problem or as general nutritional supplements. Among useful dietary supplements are dosage units of calcium citrate, orally administered in solid or liquid form (U.S. Pat. Nos. 4,772,467, 4,814,177, and 4,851,221; each patent herein incorporated by reference). Oral administration of calcium citrate as a nutritional supplement both modestly increases levels of urinary citrate and provides bioavailable calcium. By modestly increasing levels of urinary citrate, administration of calcium citrate counters calcium nephrolithiasis (i.e., formation of calcium-containing kidney stones). Furthermore, calcium is more readily absorbed when administered as calcium citrate than as calcium carbonate, i.e., the administration of calcium citrate provides calcium that is more bioavailable. Improved absorption of calcium allows more effective treatment of calcium-deficiency conditions like osteoporosis.

In U.S. Pat. No. 6,287,607, Pak et al., espoused a single compound with discrete empirical formula of potassium calcium citrate in a tablet formulation, that enjoyed bulk density of 0.8-1.3 g/cc and molar ratio of 1:1:1 or 4:1:2. The '607 patent also taught that a tablet formulation would counter kidney stone formation and bone loss based on single dose bioavailability studies.

Potassium citrate is widely used for the prevention of kidney stone formation. It has been shown to be effective in increasing urinary citrate, which is well known to retard the formation of calcium-containing kidney stones. Thus, this citrate salt of potassium has regulatory approval for the prevention of kidney stones containing calcium oxalate, the most common constituent of stones (Pak et al., 1985, *J. Urol.* 134:11-19). Potassium citrate is also an effective alkalinizing agent (Sakhaee et al., 1991, *J. Clin. Endo. Metab.* 72:396-400). By increasing the pH of urine, this treatment also prevents uric acid stones that have a tendency to form in relatively acidic urine.

There is emerging evidence that alkali delivered into the body by potassium citrate may protect against bone loss. Potassium citrate treatment has been shown to prevent calcium loss into urine (Sakhaee et al., 1991, *J. Clin. Endo. Metab.* 72:396-400) and to increase bone density (Pak et al., 2001, *J. Urol.* 168:31-34). A typical dose of potassium citrate is 20 mEq (20 mmol) twice daily.

Calcium supplementation is also widely recognized to be a linchpin for countering bone loss that occurs following menopause. It works by increasing the level of calcium in the blood by providing sufficient calcium to be absorbed from the bowel. This rise in blood calcium then suppresses the secretion of parathyroid hormone that cause bone destruction, preventing bone loss. Calcium citrate and calcium carbonate are two widely used calcium supplements for this purpose. Calcium citrate is believed to be preferable, because it is generally better absorbed (Heller et al., 2000, *J. Clin. Pharmacol* 40:1237-1244). Moreover, calcium citrate supplementation modestly increases urinary citrate, an inhibitor of kidney stone formation; thus, the risk of stone formation that might rise from calcium supplementation is thought to be low from this supplementation. Some patients with calcium oxalate stones have high urinary oxalate from absorbing too much oxalate from the bowel. Calcium citrate may be helpful by binding oxalate and preventing its absorption. A typical dose of calcium citrate for the prevention of bone loss is 400-500 mg calcium given twice daily (Ruml et al., 1999, *Am. J. Therap.* 6:303-331).

While prior art teaches the use of calcium supplementation, it does not do so for a powder formulation of potassium calcium citrate as mixtures of pure chemical salts having efficacy for the treatment and prevention of kidney stones and osteoporosis. In U.S. Pat. No. 6,680,305, a single compound with unique formula as a tablet formulation was disclosed. The compound had a molar ratio of 1:1:1 for potassium, calcium and citrate. Another compound had a molar ratio of 4:1:2. As discrete entities, they had a bulk density of 0.8 to 1.3 g/cc. The invention disclosed herein relates to a modification of potassium calcium citrate that is an improvement of tablet formulations of U.S. Pat. No. 6,680,305.

In U.S. Pat. Nos. 6,319,490; 6,719,963; and 6,908,909, liquid oral compositions comprising a calcium compound and an acidulant are disclosed. The '490, '963, and '909 patents deal with adding calcium salt to acidic beverage to prevent erosion of teeth. The product contains no potassium, an essential ingredient to achieve the benefits of the present invention. The pH range disclosed in the patents is 3.5-4.5, whereas that of the present invention is higher; ~4.5 to ~6. Thus, unlike the present invention, the teachings of this patent family do not provide an alkali load to the extent that the composition of the present invention does so.

U.S. Pat. No. 6,680,305 teaches physiologically acceptable aqueous solutions and methods for their use. The '305 patent deals with making a parenteral solution that has electrolytes and buffer into which drugs to fight cancer and nutrients (hydroxyethyl starch) can be added. In contrast, the present invention is orally administered.

In U.S. Patent Application Publication No. 2004/0185119, methods and compositions are disclosed for treating gastric hyperacidity while diminishing the likelihood of producing vitamin deficiency. This patent deals with oral preparation of antacid or drugs which inhibit gastric acid secretion. The objective is to reduce gastric acidity without interfering with absorption of vitamins. No particular ratio of K:Ca:citrate is discussed.

U.S. Pat. Nos. 4,871,554 and 4,722,847 disclose methods of adding calcium salt to citrus-containing fruit juices for calcium fortification of juices. An important ingredient in one patent is malic acid, and that in another is phosphate. The patents mention calcium bioavailability, but nothing of alkali load, rise in urinary citrate or stone prevention, which are the focus of our patent. No importance to the K:Ca:citrate ratio is made.

In the present disclosure, the evidence from a carefully conducted metabolic study in human beings is offered, revealing that the combination of commonly used doses of potassium citrate (20 mEq twice day) and calcium citrate (400 mg calcium twice daily), which deliver potassium and calcium at a molar ratio of 2:1, is better than calcium citrate in averting bone loss, and is better than potassium citrate in preventing kidney stone formation.

BRIEF SUMMARY OF THE INVENTION

In one aspect of the present invention, there is a composition comprising a mixture of potassium citrate, citric acid and a component selected from the group consisting of calcium carbonate, calcium hydroxide, calcium oxide and any combination thereof. In some embodiments, the mixture is a powder mixture. In some embodiments, the potassium citrate is at a level of from about 10 mEq to about 40 mEq, the calcium carbonate is at a level of from about 10 mEq to about 40 mEq, and citric acid is at a level of from about 20 mEq to about 100 mEq. Preferably, the composition comprises about 20 mEq potassium citrate, about 20 mEq calcium carbonate, and about 20 mEq citric acid. In some embodiments, the composition further comprises an additional 0.17-1.34 mEq of citrate in the form of citric acid. The composition may further comprises a sweetener. Where a sweetener is used, the sweetener may be an artificial sweetener. In some embodiments, the composition is in the form of a solution. In cases where the composition is in the form of a solution, the solution may be an aqueous solution. Other forms are possible, for example, the composition may be in the form of a suspension.

In another aspect of the present invention there is a powder mixture comprising potassium citrate, calcium carbonate and citric acid which when dissolved in water yields an aqueous solution of potassium, calcium and citrate at a molar ratio of potassium:calcium:citrate in a range of 2:1:1.33 to 2:1:2.67. In some embodiments, the potassium citrate is at a level of from about 10 mEq to about 40 mEq, the calcium carbonate is at a level of from about 10 mEq to about 40 mEq, and citric acid is at a level of from about 20 mEq to about 100 mEq. Preferably, the powder mixture comprises about 20 mEq potassium citrate, about 20 mEq calcium carbonate, and about 20 mEq citric acid. In some embodiments, the composition comprises an additional 0.17-1.34 mEq of citrate in the form of citric acid. Preferably, the powder mixture has a molar ratio of potassium:calcium:citrate of 2:1:1.33.

In another aspect of the present invention there is a method of treating or preventing osteoporosis or kidney stones or both in an animal comprising the administration of a composition comprising a mixture of potassium citrate, citric acid and a component selected from the group consisting of calcium carbonate, calcium hydroxide, calcium oxide and any combination thereof, said composition having a molar ratio of potassium:calcium:citrate ranging from 2:1:1.33 to 2:1:2.67. Preferably, the animal to which the composition is administered is human. In those cases where the composition is administered to a human, the human is preferably a postmenopausal woman. In some embodiments, the administration comprises oral administration. In some embodiments, the animal to which the composition is administered has chronic diarrheal syndrome. Preferably, the composition has a molar ratio of potassium:calcium:citrate of 2:1:1.33.

In another aspect of the present invention, there is a method of treating or preventing osteoporosis or kidney stones or both in an animal comprising the administration of a composition comprising a mixture of potassium citrate and calcium citrate having a molar ratio of potassium:calcium:citrate ranging from 2:1:1.33 to 2:1:2.67. Preferably, the animal to which the composition is administered is human. In those cases where the composition is administered to a human, the human is preferably a postmenopausal woman. In some embodiments, the administration comprises oral administration. In some embodiments, the animal has chronic diarrheal syndrome.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

As used herein, "a" or "an" means one or more. Unless otherwise indicated the singular encompasses the plural and the plural encompasses the singular.

As used herein, the term "animal" includes both human animal and non-human animals.

As used herein, "preventing" as the term is associated with a medical condition, disease state or symptom is defined as delaying onset or averting onset of the medical condition, disease state or symptom.

As used herein the term "treating" means improving at least one symptom or condition.

Careful studies have been completed in human subjects kept on a constant diet, to examine the effects on stone formation and calcium and bone metabolism of customary doses of potassium citrate and calcium citrate. Results clearly show that the combined treatments are better than either drug alone, in countering stone formation and bone loss. The doses of potassium citrate and calcium citrate used in these studies delivered potassium and calcium at a molar ratio of 2:1.

The present invention teaches a modification of potassium calcium citrate (PCC) therapy which removes disadvantages of tablet formulations of potassium calcium citrate. The modification promotes the use of a powder mixture of potassium citrate and calcium citrate that dissolves rapidly and fully, permitting ingestion as a liquid. Some patients prefer to drink a liquid preparation rather than swallow tablets. The rapidity with which the powder formulations dissolved overcomes the problem of somewhat poor solubility of tablet formulations of potassium calcium citrate.

Detailed laboratory experiments show that a powder mixture can be prepared which, when dissolved, yields exactly the same amount of potassium, calcium and citrate, as delivered by usual doses of potassium citrate and calcium citrate (molar ratio of 2:1:1.33 for potassium, calcium and citrate) used in clinical situations. By adding a slight excess of citric acid, the powder can be dissolved more rapidly with bubbling, and the taste can be turned from flat to slightly tart however desired. Whether given as a solid preparation or as a powder mixture (to be solubilized before administration), the end products (as solubilized ionic constituents of potassium, calcium and citrate) released into the gastric lumen should be the same. A slight excess of citrate, if added to powder preparations, is simply metabolized, confers negligible calories, and does not alter the acid-base status or physiological action. In the preferred embodiment, the composition is administered orally as an aqueous solution; however, other forms of administration and other forms of the composition known to those skilled in the art (e.g., suspensions, or solid dosage forms such as tablets, etc.) are also part of the present invention.

Data are presented demonstrating that potassium calcium citrate would be particularly useful in preventing stone formation and averting bone loss that might develop in subjects consuming a high meat diet, patients with persistent diarrhea due to various bowel diseases, and early postmenopausal women who need calcium supplements for prevention of bone loss but who are at risk for kidney stones.

Example 1

Metabolic Studies on Prevention of Kidney Stone Formation

A total of eighteen postmenopausal women without kidney stones underwent four phases of study chosen in random order while they were kept on a constant diet in a metabolic ward. Lasting two weeks each, the four phases comprised: potassium citrate (Urocit-K®) 20 mEq twice daily, calcium citrate (Citracal®) 400 mg calcium twice daily, both potassium citrate and calcium citrate at same dosages, and placebo. During last two days of each phase, urine was collected in 24-hour pools for biochemistry and stone risk factors. The combined treatment with potassium citrate and calcium citrate from this metabolic study is equivalent to treatment with potassium calcium citrate as embodied by this invention, since the amount of calcium and potassium conferred by combined treatment was about the same as the intended dose of the object of this invention.

Figure 1:
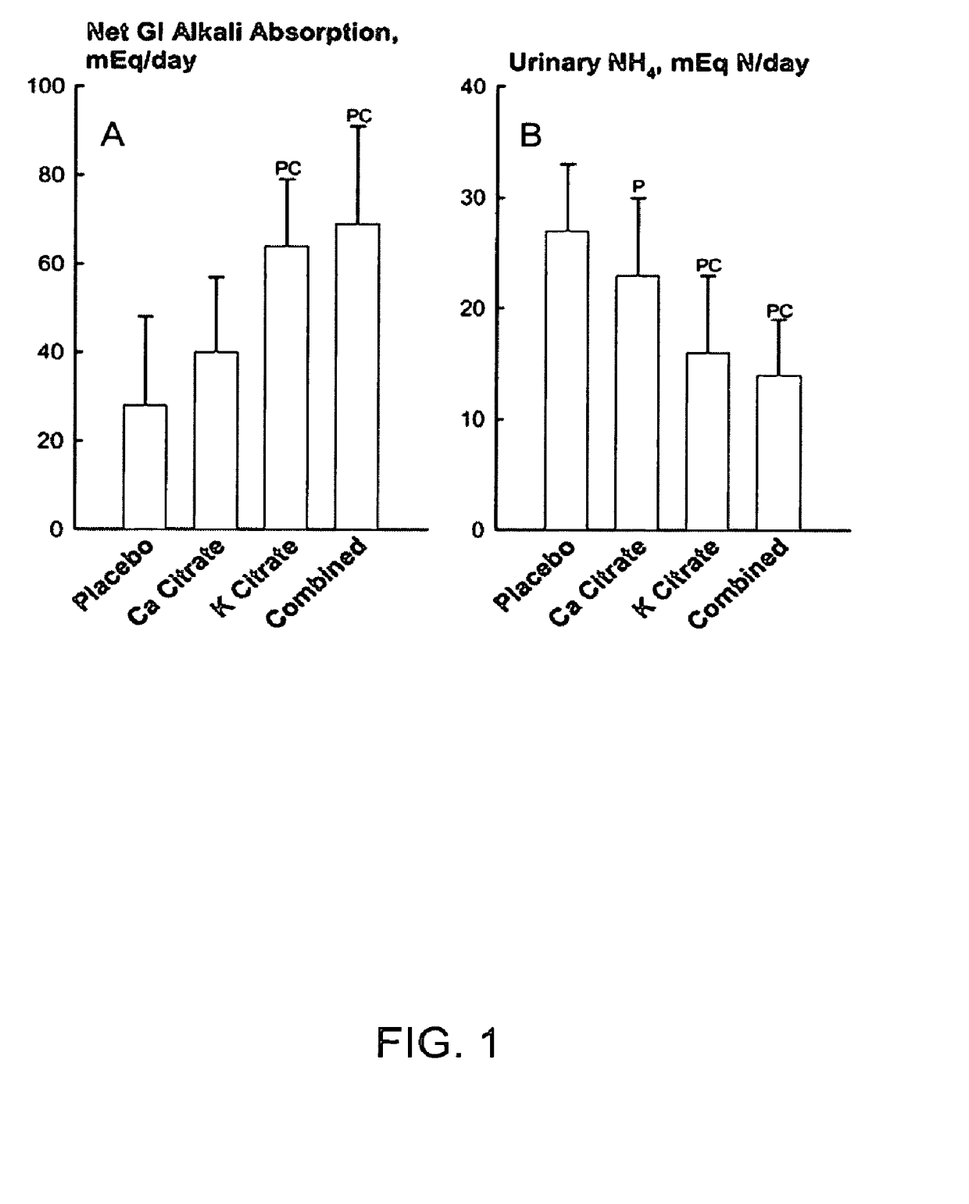
FIG. 1 graphically illustrates the delivery of alkali load; (A) net GI alkali absorption, (B) urinary ammonium, for various compositions, including that of the present invention.

Provision of alkali load. The ability of calcium citrate and potassium citrate alone and in combination to provide an alkali load was ascertained from changes in the net gastrointestinal absorption of alkali and urinary ammonium from the placebo phase (FIG. 1). (In FIGS. 1-6 the vertical bars extending past each block indicate standard deviation; significant difference from placebo is indicated by "P", that from calcium citrate by "C" and that from potassium citrate by "K", the mixed identifiers indicates significant difference from all the species identified). If an alkali load is delivered, the net gastrointestinal absorption of alkali (calculated from urinary electrolytes) increases and urinary ammonium decreases (as a normal response of kidneys to alkali). The treatment with calcium citrate marginally increased net gastrointestinal absorption of alkali and slightly but significantly decreased urinary ammonium, suggesting that calcium citrate provides a mild-modest alkali load. Potassium citrate significantly and substantially increased the net gastrointestinal absorption of alkali and reduced urinary ammonium, indicating delivery of a substantial alkali load. Largest changes were produced by combined treatment, supporting the view that addition of calcium citrate enhances the alkali load delivered by potassium citrate.

Figure 2:
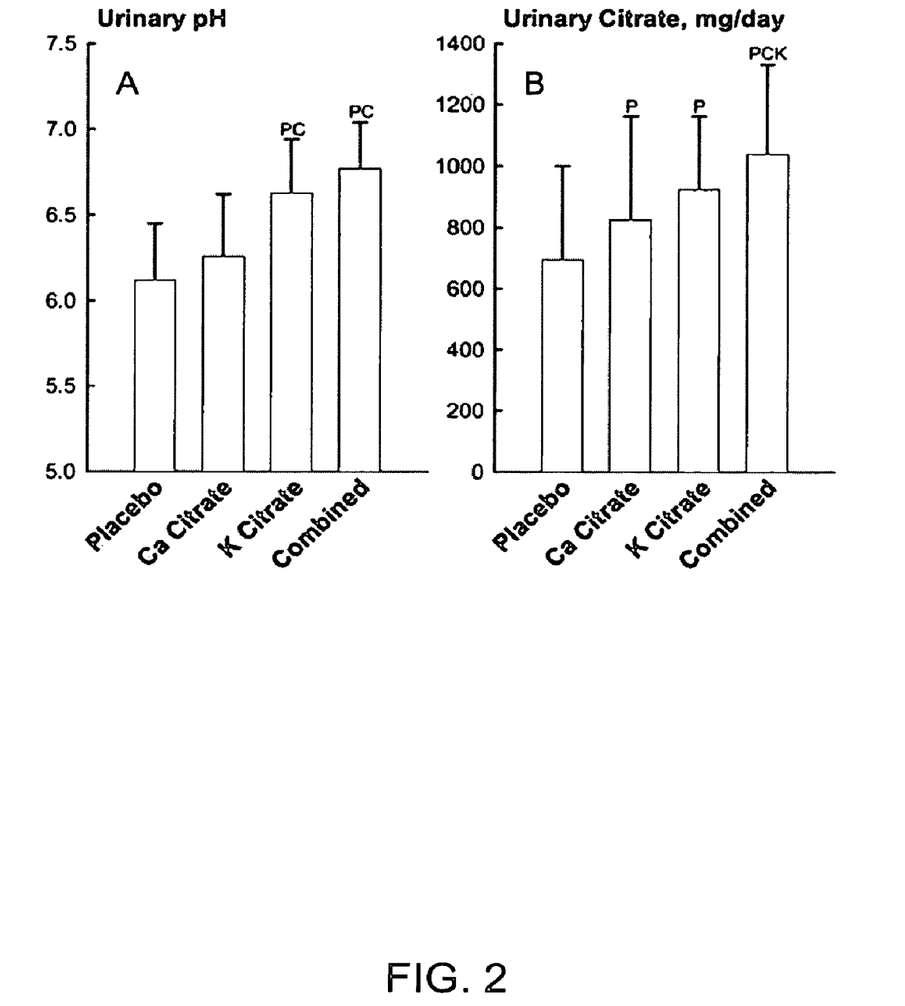
FIG. 2 graphically illustrates (A) urinary pH and (B) urinary citrate levels for various compositions, including that of the present invention.

Effect on urinary stone risk factors. Urinary pH, a measure of urinary alkalinity, increased marginally with calcium citrate, significantly and substantially rose with potassium citrate, and even more so when both salts were given (FIG. 2). Urinary citrate also increased in the same direction. These changes were due to, or represent response of the kidneys to, alkali load.

Figure 3:
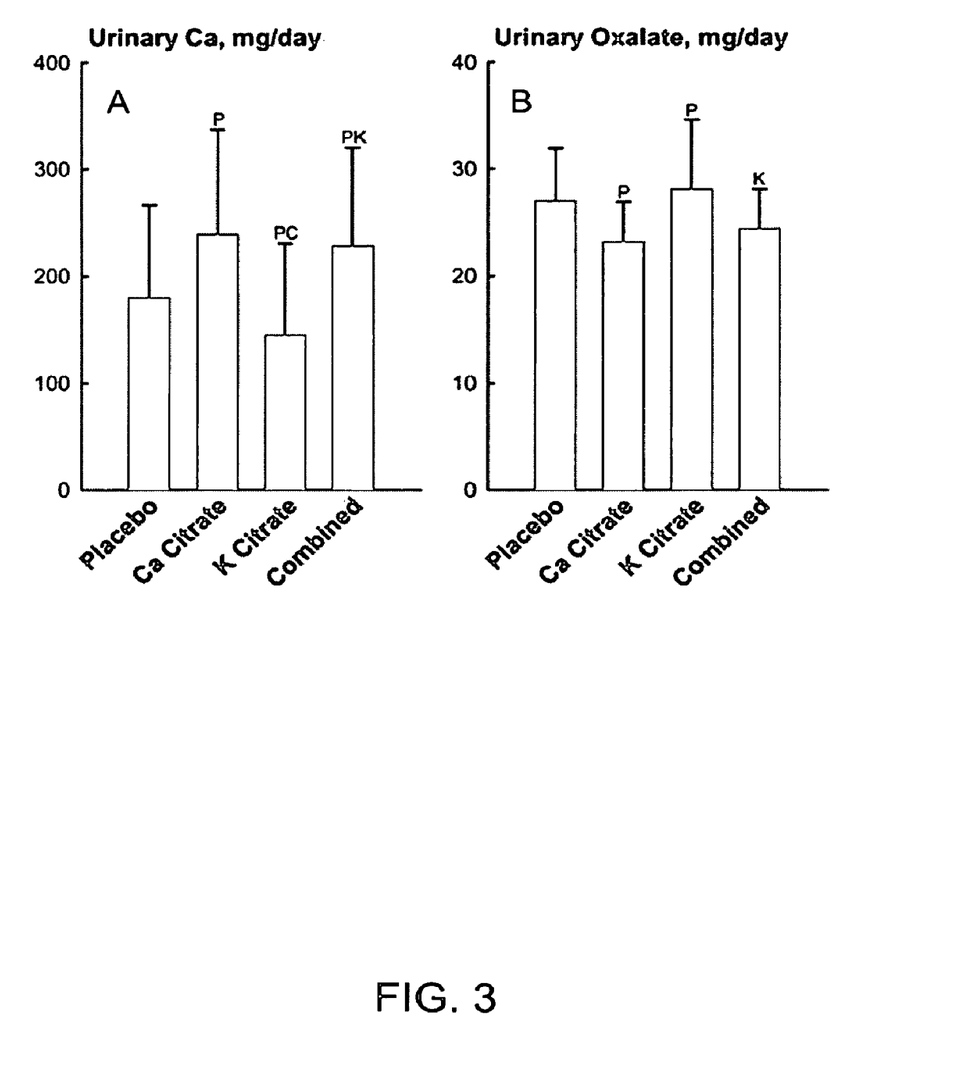
FIG. 3 graphically illustrates (A) urinary calcium and (B) urinary oxalate levels for various compositions, including that of the present invention.

Urinary calcium increased during calcium citrate treatment (owing to absorption of calcium from the bowel), but decreased with potassium citrate treatment (due to the kidney's response to the alkali load) (FIG. 3). It was also increased during combined treatment (with a slightly lower mean value from calcium citrate alone). Urinary oxalate decreased significantly with calcium citrate and marginally with combined treatment, as a result of the binding of oxalate by calcium in the bowel. It was unaffected by potassium citrate.

Figure 4:
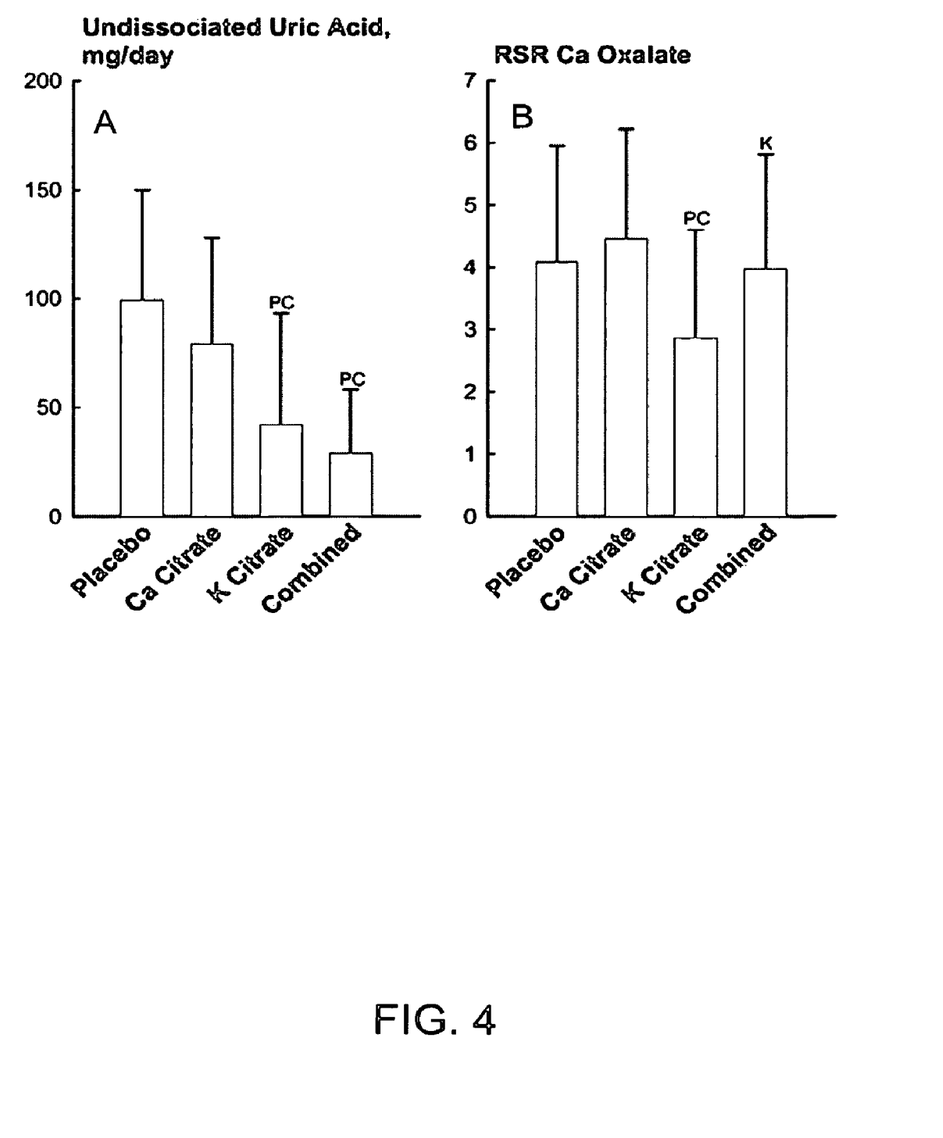
FIG. 4 graphically illustrates (A) undissociated uric acid and (B) relative saturation ratio levels for various compositions, including that of the present invention.

Effect on urinary saturation of stone-forming salts. Urinary content of undissociated (non-ionized) uric acid decreased progressively with treatment, with the most prominent decline occurring with combined treatment (FIG. 4). This form of uric acid is sparingly soluble in urine, accounting for uric acid stone formation. The above changes were largely due to the rise in urinary pH that increased the dissociation of uric acid to an ionized form, making uric acid more soluble and thereby rendering less likely the formation of uric acid stones. Urinary saturation of calcium oxalate declined with potassium citrate, due to a reduction in urinary calcium and rise in citrate (which reduced ionized calcium by complexing calcium). It increased marginally with calcium citrate treatment, since the rise in urinary calcium was not completely overcome by the decline in urinary oxalate. However, the urinary saturation of calcium oxalate was unchanged with combined treatment (due to a slightly smaller rise in urinary calcium and greater rise in urinary citrate).

Conclusion. The combined treatment, resembling potassium calcium citrate, confers more alkali load than either component alone, and thereby produces the largest rise in urinary pH and citrate. The combined treatment increases urinary calcium but decreases urinary oxalate, resembling the action of calcium oxalate, and is most effective in preventing uric acid stone formation. Additionally, it does not alter the saturation of calcium oxalate, the most common constituent of kidney stones, and probably confers inhibition against formation of calcium-containing kidney stones, by increasing urinary citrate, an "inhibitor" of stone formation. It is advantageous over calcium citrate alone, since it not only provides absorbable calcium, but also confers an alkali load, increases urinary citrate and inhibitor activity and dramatically enhances the solubility of uric acid, without changing the saturation of calcium oxalate, Additionally, it is advantageous over potassium citrate alone, since it permits calcium supplement to be given without increasing urinary saturation of calcium oxalate, produces an even greater rise in urinary citrate and inhibitor activity, and makes uric acid even more soluble.

Example 2

Metabolic Studies on Preventing Bone Loss

In the same study involving the identical subjects described in Example 1, the effect on bone metabolism of potassium citrate, calcium citrate, and combination of the two was examined. During the last two days of each two-week phase, serum and 24-hour urine samples were collected for assessment of calcium metabolism, alkali load, and bone turnover markers.

Figure 5:
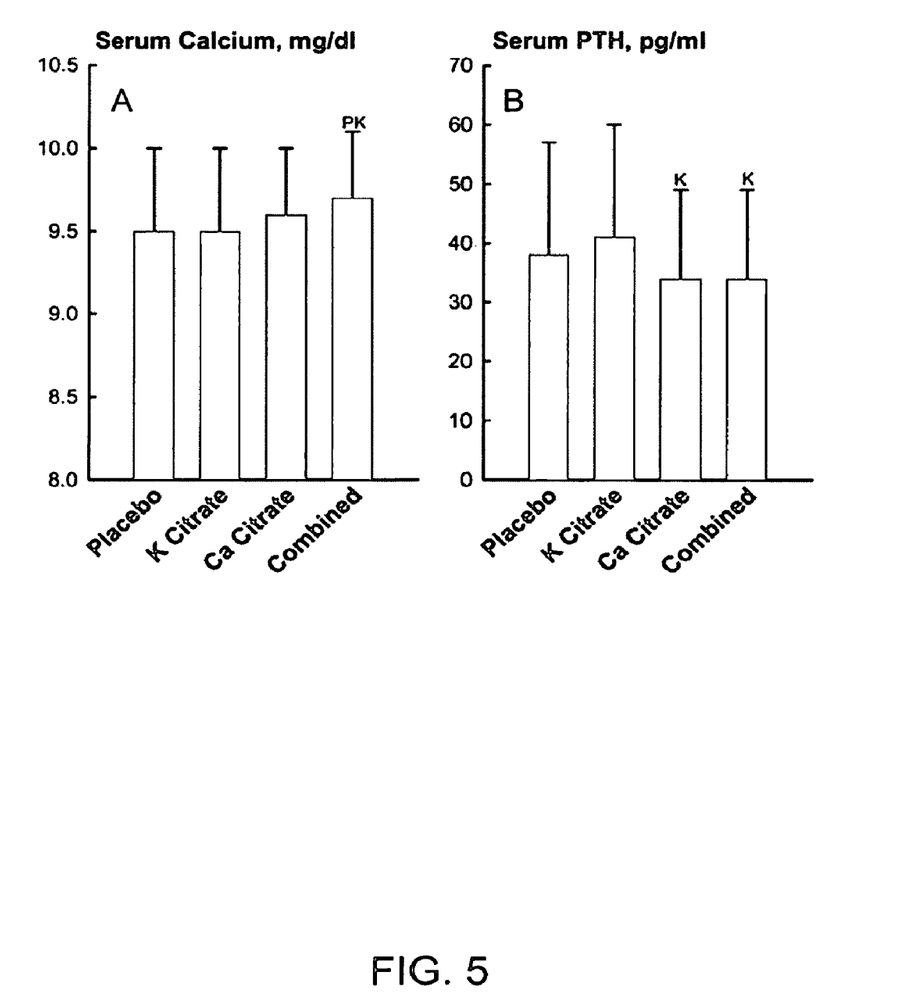
FIG. 5 graphically illustrates (A) serum calcium and (B) serum parathyroid hormone for various compositions, including that of the present invention.

Serum calcium and parathyroid hormone. Serum calcium and parathyroid hormone did not change with potassium citrate treatment (FIG. 5). Serum calcium increased slightly, and serum parathyroid hormone significantly decreased with calcium citrate. The combined treatment (resembling potassium calcium citrate) significantly increased serum calcium and marginally decreased serum parathyroid hormone.

Figure 6:
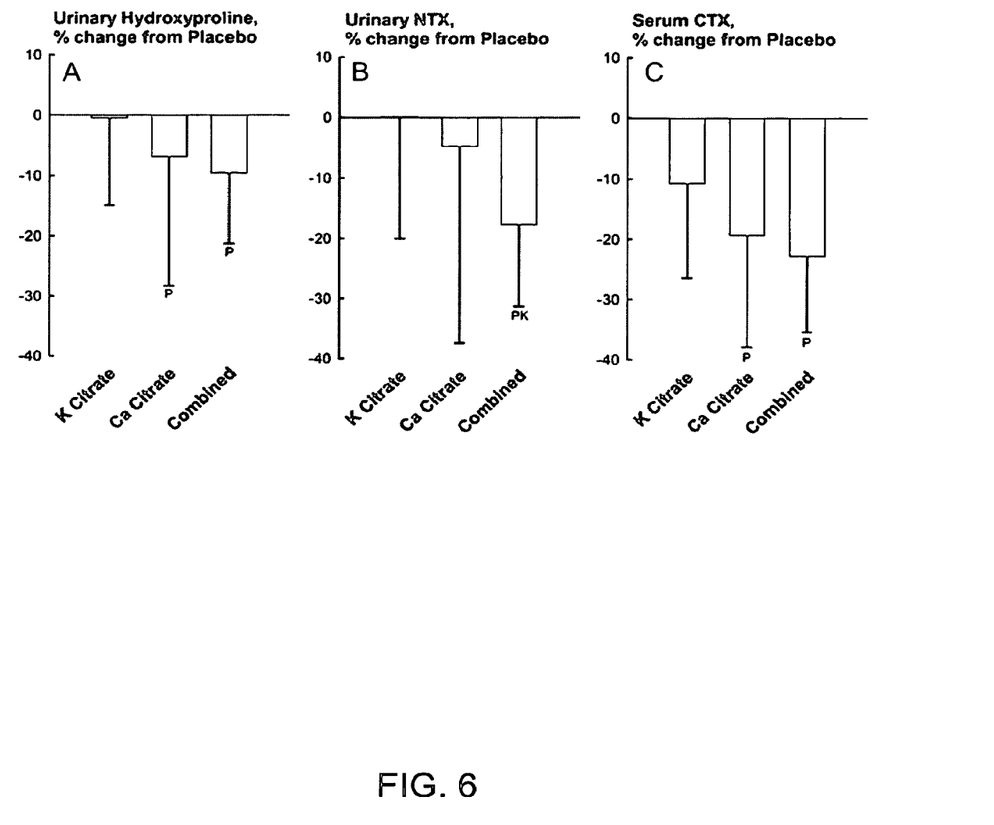
FIG. 6 graphically illustrates the percent change from placebo of (A) urinary hydroxyproline, (B) urinary N-telopeptide, and (C) type I collagen telopeptide for various compositions, including that of the present invention.

Markers of bone turnover. The effect of treatment on bone resorption (destruction) was evaluated from urinary hydroxyproline, urinary N-telopeptide, and serum type 1 collagen C-telopeptide. These bone-derived substances are called markers of bone resorption, since they are elevated in states of high bone destruction. In FIG. 6, the changes in these markers from the placebo phase are displayed. The decline in the markers was generally least prominent for potassium citrate, intermediate for calcium citrate, and most marked for the combined treatment (resembling potassium calcium citrate).

Figure 7:
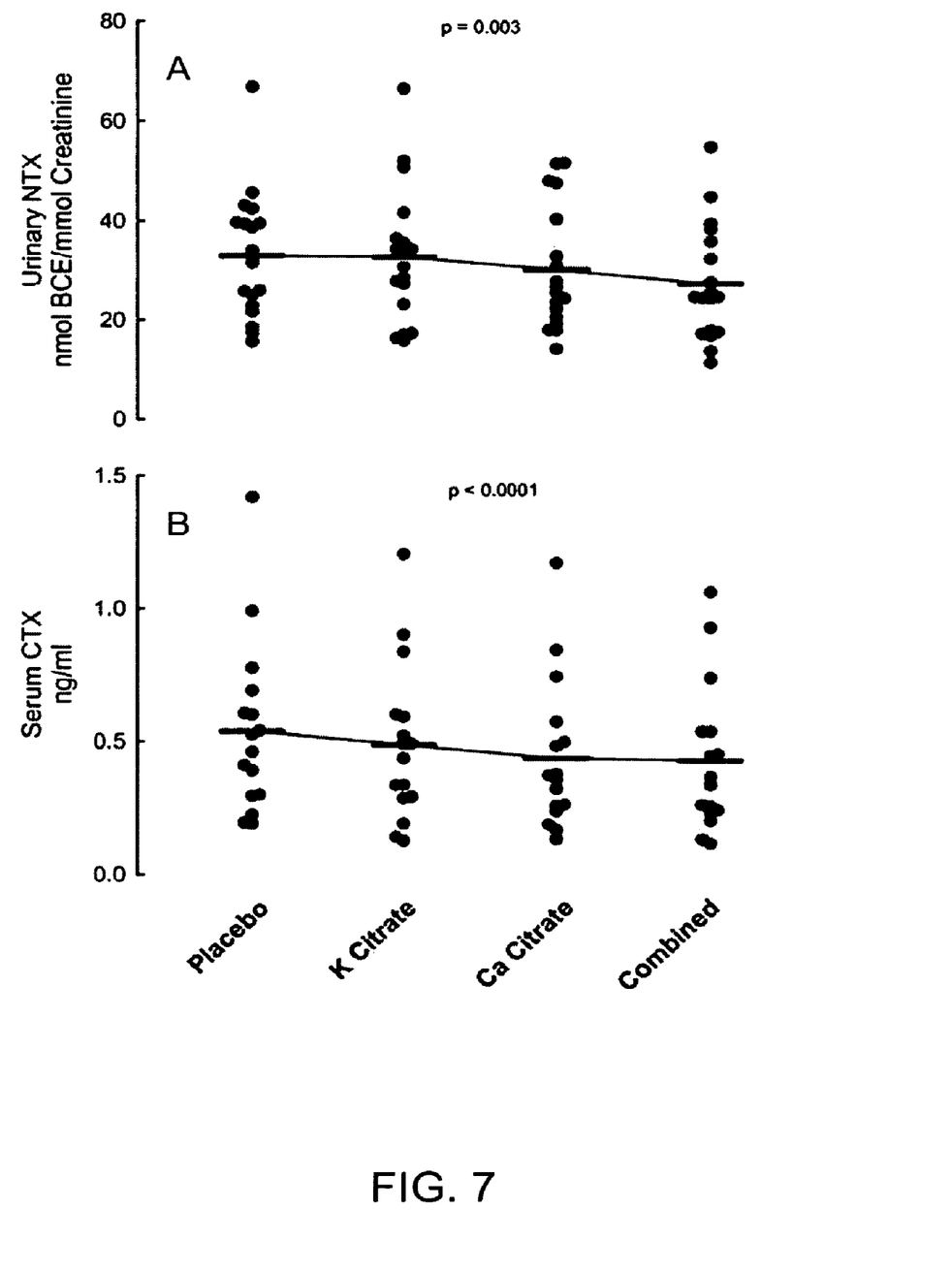
FIG. 7 graphically illustrates the trends in (A) urinary NTX and (B) serum CTX indicative of the trends in bone resorption as the treatment changed from placebo to potassium citrate to calcium citrate to combined treatment.

Statistical differences among the four treatment phases were analyzed by comparisons between pairs of treatment, by use of contrasts from the ANOVA models. As the treatment changed from placebo to potassium citrate to calcium citrate to combined treatment, a significant trend was observed for urinary N-telopeptide and serum type I collagen C-telopeptide (FIG. 7).

Conclusion. The combined treatment with potassium citrate and calcium citrate suppresses parathyroid function, as does calcium citrate. However, unlike calcium citrate, the combined treatment confers alkali load, as does potassium citrate. The combined treatment suppresses bone resorption more effectively than either potassium citrate or calcium citrate alone.

Example 3

Conditions Amenable to Treatment with Potassium Calcium Citrate

High meat diet. The consumption of a high animal protein diet such as the Atkins' diet commonly taken for weight control, may increase the risk of kidney stones and bone loss. In a carefully conducted study in subjects consuming a constant diet, the Atkins' diet was shown to produce a marked acid load, nearly double urinary calcium, and lower urinary pH (making urine more acid) and citrate (inhibitor of calcium stone formation) (Reddy et al., 2002, Amer. J. Kid. Dis., 40: 265-274). Thus, the urine became more supersaturated with respect to stone-forming salts, making the formation of uric acid and calcium oxalate stones more likely. At the same time, the calcium balance turned more negative, because the intestinal calcium absorption was not changed even though urinary calcium increased.

Chronic diarrheal syndrome. From the Stone Clinic of the inventors (CYCP and KS), 71 patients with chronic diarrheal syndrome were identified. The majority of these patients suffered from calcium oxalate stones. However, 21% of them had uric acid stones. All patients had persistent diarrhea from various conditions affecting the bowel (Table 1). The most common cause was Crohn's disease found in 23% of patients, followed next by intestinal bypass for morbid obesity in 17%. Gastrectomy and irritable bowel syndrome accounted for 14% each, and ulcerative colitis 7%. Minor causes of persistent diarrhea were certain drugs, pancreatitis (inflammation of the pancreas), small bowel resection or atresia, severe peptic ulcer, and radiation treatment that inadvertently affected the bowel. In 10% of cases, the cause of persistent diarrhea was not evident.

A 24-hour urine sample was collected from above patients during their random (customary) diet and during restricted diet when they were instructed to avoid excess intake of calcium, salt and oxalate. The samples were analyzed for constituents that are involved in stone formation (called stone risk factors) as shown in Table 2. The data shows the stone risk factors and one standard deviation for the sample. Urinary pH was low, due to loss of alkali in the diarrheal fluid and resulting acid load to the body. This undue acidity of urine increased the amount of uric acid in non-charged (undissociated, poorly soluble) form, accounted for uric acid stones. Urinary oxalate was high normal, due to stimulation of oxalate absorption from the bowel known to occur in some bowel diseases. Urinary citrate (a substance that inhibits formation of calcium oxalate stones) was low, from the response of the kidneys to the acid load. As a result, urine became more supersaturated with respect to calcium oxalate, accounting for calcium oxalate stones. Urinary calcium and magnesium tended to be low normal, consistent with the impairment in intestinal absorption of these divalent cations (doubly charged positive ions).

TABLE 1

Causes of Chronic Diarrheal Syndrome

| | Number of Subjects | Percent of Subjects |
| --- | --- | --- |
| Crohn's disease | 16 | 23 |
| Intestinal bypass | 12 | 17 |
| Gastrectomy | 10 | 14 |
| Irritable bowel syndrome | 10 | 14 |
| Ulcerative colitis | 5 | 7 |
| Drugs (antacid, quinidine) | 3 | 4 |
| Pancreatitis | 3 | 4 |
| Small bowel resection/atresia | 3 | 4 |
| Ulcers | 1 | 1 |
| Radiation therapy | 1 | 1 |
| Unknown | 7 | 10 |

TABLE 2

Urinary Stone Risk Factors in Chronic Diarrheal Syndrome

| | Random Diet | | | Restricted Diet | | | |
|---|---|---|---|---|---|---|---|
| | No. Patients | Risk Factor | 1 S.D. | No. Patients | Risk Factor | 1 S.D. | Normal |
| Total Volume, ml/day | 71 | 1610 ± 1105 | | 71 | 1393 ± 863 | | >2000 |
| pH | 71 | 5.66 ± 0.36 | | 71 | 5.69 ± 0.36 | | 5.5-7.0 |
| Citrate, mg/day | 58 | 229 ± 238 | | 63 | 196 ± 187 | | >320 |
| Oxalate, mg/day | 62 | 43.6 ± 33.5 | | 70 | 41.2 ± 27.1 | | <45 |
| Calcium, mg/day | 71 | 161 ± 116 | | 71 | 126 ± 90 | | 100-250 |
| Magnesium, mg/day | 69 | 64.5 ± 37.8 | | 69 | 58.6 ± 35.9 | | >60 |
| Sodium, mEq/day | 71 | 149 ± 100 | | 70 | 89 ± 55 | | <200 |
| Potassium, mEq/day | 71 | 41.5 ± 18.5 | | 71 | 36.6 ± 17.4 | | >70 |
| Uric Acid, mg/day | 71 | 478 ± 203 | | 71 | 433 ± 217 | | 400-700 |
| Phosphorus, mg/day | 69 | 860 ± 397 | | 69 | 761 ± 282 | | <1000 |

Early postmenopausal women. From epidemiological studies, stone formation in women has been shown to increase during the early postmenopausal period shortly after menopause (Heller et al., 2002, *J. Urol.*, 168: 1923-1927). This increase has been attributed to the rise in urinary calcium from the loss of the protective action of estrogen on conserving calcium in the kidneys and bone. However, bone loss is more rapid during early than late menopause, emphasizing the need for calcium supplements to prevent bone loss during the first few years after cessation of menses. While calcium carbonate has been shown to be only partially effective, calcium citrate supplement has been reported to prevent, though not increase, bone mineral density in early postmenopausal women (Ruml et al., 1999, Amer. *J. Therap.*, 6: 303-311). The problem is the concern that calcium supplements may provoke kidney stone formation, especially in women with a personal history of having had kidney stones or who have a fear of or are believed to have increased risk for kidney stones.

The overall conclusion from Examples 2 and 3. In subjects on a high meat diet and patients with chronic diarrhea who are thereby susceptible to kidney stone formation and bone loss, the combined treatment (as embodied by potassium calcium citrate in this invention) may be taken to provide alkali (to neutralize the acid load and prevent stone formation), as well as offer absorbable calcium (to help avert bone loss). Moreover, among subjects who want to take calcium supplements to counter bone loss and osteoporosis but are worried about forming kidney stones from taking them, potassium calcium citrate may be an ideal agent.

Example 4

Preparation of Powder Mixtures

Six powder mixes of potassium calcium citrate were prepared; their compositions are presented in Table 3. Calcium was provided as calcium carbonate. By adding equivalent amount of citric acid, calcium carbonate was allowed to dissolve in water or gastric juice by reacting with citric acid to form soluble calcium citrate. Potassium was provided as potassium citrate. When the premix of calcium carbonate, citric acid and potassium citrate was dissolved in water, the resulting aqueous preparations delivered the same single doses of calcium and potassium, as provided by the usual single doses of commercial calcium citrate and potassium citrate; that is, 20 mEq (400 mg) of calcium and 20 mEq of potassium, respectively. Preparation A contained just the amount of total citrate (40 mEq) to neutralize total amount of calcium and potassium cations (40 mEq). Thus, the molar ratio of Preparation A was 2:1:1.33, since each dose in 250 cc yielded 20 mmol potassium, 10 mmol calcium, and 1.33 mmol citrate (40 mEq divided by a valence of 3). The chemical composition of Preparation A was identical to a single dose of combined calcium citrate and potassium citrate treatment described in Examples 1 and 2.

Solutions B-F contained additional citric acid, with an excess of citrate over potassium and calcium of 5-40 mEq. Thus, while the molar ratio of potassium and calcium and potassium remained the same at 2:1, the citrate component of the molar ratio of potassium calcium citrate increased from 1.33 to 2.67.

TABLE 3

Composition of 6 powder preparation of potassium calcium citrate

| | Preparation | | | | | |
|---|---|---|---|---|---|---|
| | A | B | C | D | E | F |
| Citric acid•$H_2O$, g | 1.402 | 1.752 | 2.103 | 2.804 | 3.380 | 4.206 |
| Ca carbonate | 1.001 | 1.001 | 1.001 | 1.001 | 1.001 | 1.001 |
| $K_3$Citrate•$H_2O$ | 2.164 | 2.164 | 2.164 | 2.164 | 2.164 | 2.164 |
| Total Ca, mmol | 10 | 10 | 10 | 10 | 10 | 10 |
| Total Ca, mg | 400 | 400 | 400 | 400 | 400 | 400 |
| Total K, mmol | 20 | 20 | 20 | 20 | 20 | 20 |
| Citrate from CA, mEq | 20 | 25 | 30 | 40 | 48 | 60 |
| Total Citrate, mEq | 40 | 45 | 50 | 60 | 68 | 80 |
| PCC molar ratio | 2:1:1.33 | 2:1:1.5 | 2:1:1.67 | 2:1:2 | 2:1:2.27 | 2:1:2.67 |

Example 4

Identical Release of Potassium, Calcium and Citrate from Powder Formulation and Tablet Commercial Preparations of Calcium Citrate and Potassium Citrate Preparation A was dissolved in 250 mL of water containing 100 mEq of hydrochloric acid. Into the same acidified water, two tablets of Citracal (calcium citrate, 200 mg calcium per tablet, Mission Pharmacal Co., San Antonio, Tex.) and 2 tablets of Urocit-K (potassium citrate, 10 mEq per tablet, Mission Pharmacal, San Antonio, Tex.) were added, and stirred for 1 hour until full disintegration of tablets took place and both salts fully dissolved.

The solution was analyzed for potassium, calcium and citrate. Exactly the same amounts of potassium, calcium and citrate were found in the two solutions, with a variation being within experimental error. The pH was identical between the two solutions.

Example 5

Solubility and Taste of Preparations A-F

When added to 250 mL of deionized water, Solution A left a slightly cloudy fluid after 3 minutes without any settling. When added to 500 mL water, Solution A dissolved fully in 3 minutes imparting a clear solution (Table 4).

Preparations B-F dissolved rapidly in 250 mL of deionized water with bubbling (Table 4). As the citrate content increased from Preparation B-F, the powder dissolved more rapidly, with a greater elaboration of carbon dioxide (bubbling). Moreover, the taste of the solution became more tart, and pH decreased. All solutions were clear and free of smell.

TABLE 4

Solubility of Preparations A-F

| | Preparation | | | | | |
|---|---|---|---|---|---|---|
| | A | B | C | D | E | F |
| Volume of water, cc | 500 | 250 | 250 | 250 | 250 | 250 |
| Rapidity of dissolution, min | 3 | <1 | <1 | <0.5 | Immediate | Immediate |
| Bubbling | No | Some | Some | Some | Some | Some |
| Clarity of solution | Yes | Yes | Yes | Yes | Yes | Yes |
| Smell | No | No | No | No | No | No |
| Taste | Flat | Tasteless Or flat | Tasteless | Tart + | Tart ++ | Tart +++ |
| Aftertaste | None | None | None | None | None | None |
| pH | 6.04 | 5.33 | 4.94 | 4.50 | 4.30 | 4.05 |

Preparation B was tested for tolerance in 9 subjects who drank a full dose (250 mL). There were no complaints of upper abdominal discomfort or gas. One subject noted that one bowel movement was soft. One felt the preparation tasted flat.

To Preparations C and D, a flavoring and artificial sweetener were added; they were enclosed in convenient dose packets. Subjects found the preparation easy to prepare (in 250 mL water) and palatable. Some subjects preferred Preparation C for its lack of tartness, while others liked Preparation D better for is slight tartness.

Calcium hydroxide or another suitable calcium salt may be substituted for calcium carbonate (to be used in combination with citric acid to form soluble calcium citrate), although calcium carbonate is preferred. Alternatively, a powder mix of potassium citrate and calcium citrate can be used directly, with an excess of citric acid added to increase solubility.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating or preventing osteoporosis or kidney stones or both in an animal at risk of or predisposed to developing osteoporosis or kidney stones comprising:
    obtaining a dose of a composition comprising a mixture comprising from about 10 mEq to about 40 mEq potassium citrate, about 10 mEq to about 40 mEq calcium carbonate, and about 20 mEq to about 100 mEq citric acid; and
    administering the dose to the animal;
wherein osteoporosis and/or kidney stones are prevented or treated in the animal.

2. The method of claim 1, wherein said administration comprises oral administration.

3. The method of claim 2, wherein the composition is further defined as an aqueous solution.

4. The method of claim 3, further comprising preparing the aqueous solution by dissolving the dose comprising the mixture in water.

5. The method of claim 4, wherein the solution elaborates carbon dioxide upon dissolution.

6. The method of claim 1, wherein the mixture comprises potassium:calcium:citrate in a molar ratio range of from 2:1:1.33 to 2:1:2.67.

7. The method of claim 1, further comprising administering two doses of the composition per day.

8. The method of claim 1, where the mixture is in the form of a tablet.

9. The method of claim 1, where the mixture is in the form of a powder.

10. The method of claim 1, wherein the animal is human.

11. The method of claim 10, wherein the human is a post-menopausal woman.

12. The method of claim 1, wherein the animal has chronic diarrheal syndrome.

13. The method of claim 6, wherein the composition has a molar ratio of potassium:calcium:citrate of 2:1:1.33.

14. The method of claim 1, wherein said composition comprises about 20 mEq potassium citrate, about 20 mEq calcium carbonate, and about 20 mEq citric acid.

15. The method of claim 1, wherein said composition further comprises a sweetener.

16. The method of claim 15, wherein said sweetener is an artificial sweetener.

17. A method of treating osteoporosis or kidney stones or both in an animal at risk of or predisposed to developing osteoporosis or kidney stones comprising:

obtaining a dose of a composition comprising a mixture comprising from about 10 mEq to about 40 mEq potassium citrate, about 10 mEq to about 40 mEq calcium carbonate, and about 20 mEq to about 100 mEq citric acid; and administering the dose to the animal;

wherein osteoporosis and/or kidney stones are treated in the animal.

18. The method of claim 17, wherein the animal is human.

19. The method of claim 18, wherein the human is a post-menopausal woman.

20. The method of claim 17, wherein said administration comprises oral administration.

21. The method of claim 17, wherein the animal has chronic diarrheal syndrome.

22. The method of claim 6, wherein the composition has a molar ratio of potassium:calcium:citrate of 2:1:1.33.

23. The method of claim 17, wherein the mixture comprises potassium:calcium:citrate in a molar ratio range of from 2:1:1.33 to 2:1:2.67.

24. The method of claim 17, wherein said composition comprises about 20 mEq potassium citrate, about 20 mEq calcium carbonate, and about 20 mEq citric acid.

25. The method of claim 17, where the mixture is in the form of a tablet.

26. The method of claim 17, where the mixture is in the form of a powder.

* * * * *